United States Patent [19]

Genser

[11] Patent Number: 4,738,295
[45] Date of Patent: Apr. 19, 1988

[54] METHOD AND APPARATUS FOR EVAPORATING A FLUID IN A ROTATING VACUUM EVAPORATION SYSTEM

[76] Inventor: Hans G. Genser, Detwang 17, D-8803 Rothenburg o.d.T, Fed. Rep. of Germany

[21] Appl. No.: 847,221

[22] Filed: Apr. 2, 1986

[30] Foreign Application Priority Data

Apr. 2, 1985 [DE] Fed. Rep. of Germany ....... 3511981

[51] Int. Cl.⁴ .......................... B01D 1/22; B01D 3/08
[52] U.S. Cl. ......................................... 159/6.1; 159/7; 159/11.2; 159/23; 159/44; 159/49; 73/313; 73/454; 202/181; 202/205; 202/206; 202/238; 203/1; 203/89; 203/DIG. 2; 203/DIG. 18; 338/33
[58] Field of Search ................. 203/1, 89, 91, DIG. 2, 203/DIG. 7, DIG. 18; 159/6.1, 7, 11.2, 13.1, 23, 44, 43.1, 49; 202/181, 238, 236, 206, 205; 422/101, 102; 73/313, 454; 177/207; 338/33

[56] References Cited

U.S. PATENT DOCUMENTS

| 1,366,465 | 1/1921 | Kells | 202/206 |
| 1,379,631 | 5/1921 | Kells | 202/206 |
| 1,975,222 | 10/1934 | Brown | 203/1 |
| 2,554,425 | 5/1951 | Storment | 203/1 |
| 2,762,761 | 9/1956 | Stanley et al. | 202/206 |
| 3,039,523 | 6/1962 | Braak et al. | 159/44 |
| 3,400,747 | 9/1968 | Genser | 159/23 |
| 3,532,606 | 10/1970 | Sibert | 203/1 |
| 4,390,500 | 6/1983 | Miskinis | 202/238 |
| 4,522,684 | 6/1985 | Saito | 159/11.2 |

Primary Examiner—Wilbur Bascomb
Attorney, Agent, or Firm—Bacon & Thomas

[57] ABSTRACT

A method and apparatus of controlling a rotating vacuum evaporation system is disclosed. The rotating flask, containing the medium to be evaporated, is buoyantly supported in a liquid bath and the relative elevation between the flask and the liquid level in the bath is measured. The relative elevation is utilized as the control signal to control the addition of fluid medium to the flask, and to shut off the system when desired.

27 Claims, 2 Drawing Sheets

METHOD AND APPARATUS FOR EVAPORATING A FLUID IN A ROTATING VACUUM EVAPORATION SYSTEM

FIELD OF THE INVENTION

The present invention relates to a rotating vacuum evaporation system for treating products, including evaporating a fluid, particularly such a system which needs minimum supervision.

BRIEF DESCRIPTION OF THE PRIOR ART

Rotating vacuum evaporation systems are known in the art and, typically, such systems utilize a flask into which the fluid is placed, means to support the flask, and means to rotate the flask while it is subjected to heat. By rotating the flask, the fluid is formed into a coating on the interior surface of the flask which facilitates its evaporation. It is also known to support the flask in a liquid so as to minimize the stresses imparted to the rotational drive system. As the vapors are developed within the flask, they are withdrawn by a vacuum device. The flask may also be connected to a source of liquid to replenish the supply as it evaporates.

While such prior art systems have generally been successful, the apparatus must be continually monitored to ensure that the fluid reaches the desired concentration, to replenish the fluid as needed, and to ensure that the fluid is not totally evaporated out of the flask. Such continuous monitoring is highly labor intensive and, thus, markedly increases the costs of using the device.

Often, it is necessary to use the rotating vacuum system to concentrate a particular fluid to a specific, preselected value. Heretofore, this was achieved only by sophisticated equipment and at great expense to the user.

SUMMARY OF THE INVENTION

The present invention provides a method and an apparatus for use with a rotating vacuum evaporation system which increases the performance of the system, while decreasing the costs of using the equipment. The method and apparatus permit the user to achieve a specific concentration of a final product in the rotary flask by means of simple automatic regulation and control.

The system according to the invention buoyantly supports the rotating flask in a liquid bath while applying heat to the flask so as to evaporate the fluid within the flask. The elevation of the flask relative to the level of the liquid in the bath is determined and is utilized to control the operation of the system. The elevation of the flask relative to the level of the liquid bath is a direct measure of the weight of the contents (including the quantity of fluid) in the rotary flask, when all of the remaining parameters are kept constant. Therefore, this relative elevation can be utilized as a control value to control the supply of fluid to the flask; as a control for the specific concentration of the fluid remaining in the flask; or as a safety feature to shut off the equipment without the need for constant supervision.

The system may also be used to maintain an optimum amount of the fluid within the rotary flask to ensure that its inside surface is completely wetted by the fluid during its rotation. This allows the rotary evaporator to operate at maximum efficiency.

The elevation of the flask relative to the level of the liquid in the bath may be determined by measuring the angular position of the flask relative to a fixed support; by light beam barriers at predetermined locations; by an electrical resistor perpendicular to the liquid surface which varies the resistance with the height of the liquid; or by other means.

The present invention allows a substance to be evaporated to a specific, pre-selected value and to shut off the system when this value is reached.

DETAILED DESCRIPTION OF THE PREFERRED EMBODIMENT

Figure 1:
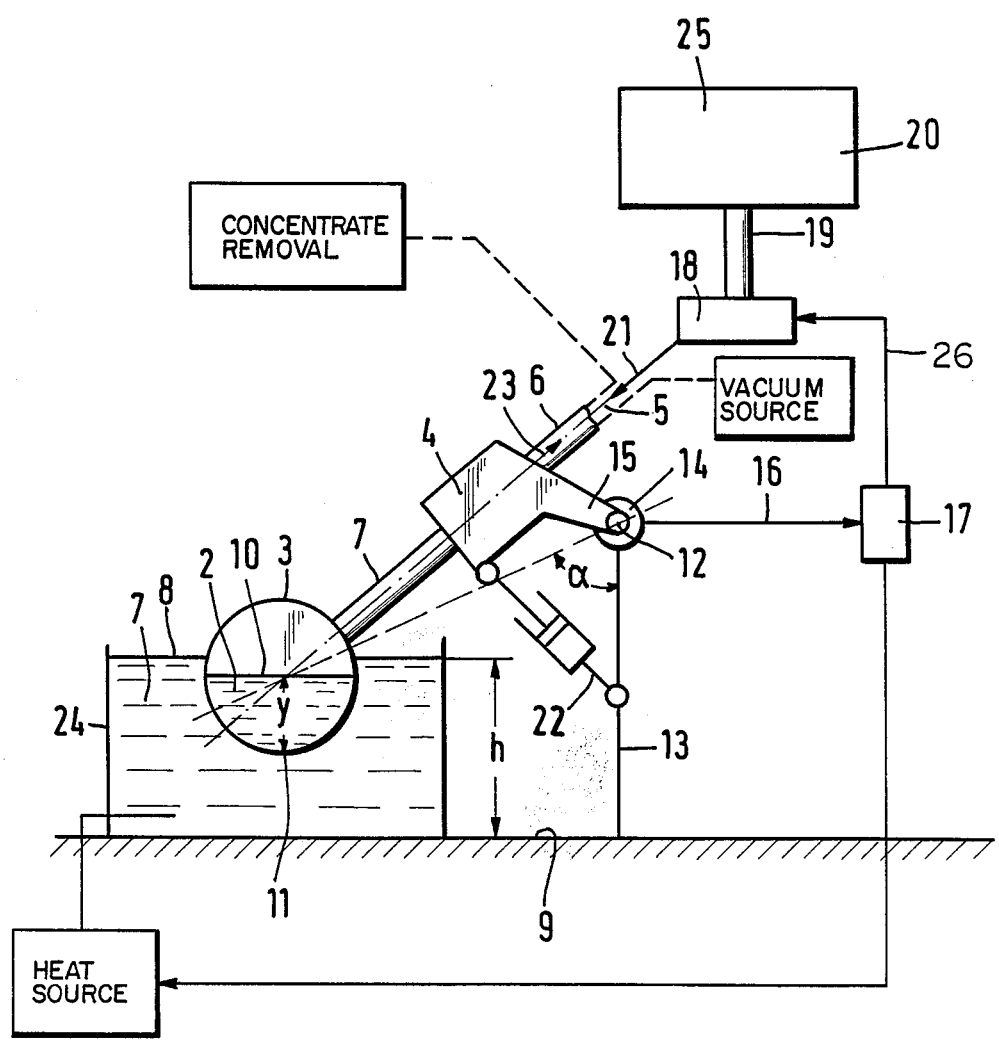
FIG. 1 is a schematic representation of a rotating vacuum evaporation system incorporating the control system according to the invention.

As schematically illustrated in the figures, the rotating vacuum evaporation system comprises a flask 3 having an axis of symmetry 5 which is connected to drive system housing 4 via tube 7. As is well known in the prior art, motor drive system 4 rotates tube 7 and the flask 3 about its axis of symmetry 5, so as to form a fluid film on the interior surface of the flask to facilitate the evaporation of the fluid.

Fluid 2 may be supplied to the interior of the flask via tube 7, coaxial tube 6 and reservoir 20. Reservoir 20 contains a storage amount 25 of the liquid 2 which may be passed therefrom through conduit 19 connected to valve 18. Valve 18 then selectively supplies the fluid to the flask through coaxial tubes 6 and 7 by the connection with line 21.

The vapor generated within the interior of flask 3 through the evaporation of fluid medium 2 is withdrawn by a known vacuum system, in the direction of arrow 23.

The flask 3 is buoyantly supported by liquid bath 1 in vessel 24. The liquid 1 is preferably water, but may be any liquid capable of transferring heat to the fluid within the flask 3. A source of heat is utilized to heat the liquid 1 to the desired temperature to effect an evaporation of the fluid 2 within flask 3.

The quantity of liquid 1 in the vessel 24 is kept constant and the height h of the surface 8 of the liquid 1 changes according to the depth of penetration of the rotary flask 3 into the liquid. Known means may be utilized to maintain the quantity of the liquid 1 constant. Such means may add a quantity to the bath 24 if there is a slight reduction due to evaporation, etc.

The elevation of the rotary flask 3 in the liquid 1 is dependent upon its mass with respect to the bath. The mass of the rotary flask includes the weight of the flask itself, the unsupported weight of the drive mechanism, and the weight of the contents of the flask. The flask contents may include the fluid medium 2 which is to be evaporated and any concentrate which is present in the flask. If the content of the flask 3 is still a viscous fluid, the mass may be defined by the distance y from the lowermost portion 11 of the flask 3 to the surface 10 of the fluid 2. Assuming all other parameters to be constant, the larger the distance y, the more deeply the rotary flask 3 will penetrate into liquid 1. However, if the fluid 2 is more concentrated, assuming the form of a paste, then it will be distributed over the inside wall of the flask 3 and a surface 10 of the fluid 2 will no longer exist.

In order to allow the flask 3 to freely penetrate into the liquid 1, the motor drive housing 4 is pivotally supported on stand 13 via arm 15 and shaft 12. Shaft 12 forms a pivot axis to enable the motor housing 4, the tube 7, the flask 3 and the fluid 2 to be buoyantly supported by the liquid 1.

An angle $\alpha$ measured between a fixed reference line, in this case stand 13, and a line passing between the pivot axis 12 and the center of flask 3, may be utilized as the control value. Obviously, as the mass of fluid 2 in flask 3 changes, thereby altering the depth of penetration of flask 3 in liquid 1, the angle $\alpha$ will also change. In order to provide a usable output signal, a rotary potentiometer 14 may be attached between the stand 13 and the housing 4. The electrical resistance of the potentiometer 14 changes as the angle $\alpha$ changes. Thus, known electrical means may be provided such that this change in electrical resistance alters an output signal. This output signal, schematically indicated at 16, may be connected to an adjustment means 17 which, in turn, is connected to valve 18 schematically indicated at 26. As noted previously, this valve controls the supply of fluid from reservoir 20. Valve 18 may be a magnetic valve or the like. Adjustment means 17 may be an electronic program device to electronically control the operation of the system.

A reference value may be set in adjustment means 17 such that, when the signal 16 from rotary potentiometer 14 reaches the reference value, valve 18 will be closed. This signal will correspond to supplying a fixed quantity of fluid from the reservoir 20 into flask 3. When the subsequent evaporation of the medium 2 in flask 3 causes a corresponding rise of the flask 3 in the liquid 1, signal 16 will cause adjustment means 17 to open valve 18 and supply a new amount of fluid medium to the flask. After the desired concentration of the fluid in flask 3 has been achieved, the evaporation is stopped and the concentrated residue is removed from the flask. The amount of fluid added to the flask is such that all or most of the inside surface of the rotary flask is wetted, thereby insuring that the flask always operates at its maximum efficiency. By systematically adding an additional amount of fluid 2, the height y from surface 10 to the lowest point 11 of the flask is maintained substantially constant. A shock absorbing device 22 may be interposed between the motor housing 4 and the stand 13 to dampen out unnecessary oscillations of the flask.

Instead of utilizing the rotary potentiometer 14, other means are possible to determine the relative elevation of the flask in the liquid bath. The height h of the liquid level of the bath 1 within vessel 24 may be determined by known measuring means, and a signal corresponding to this change in height could be utilized as the control signal.

Figure 2A:
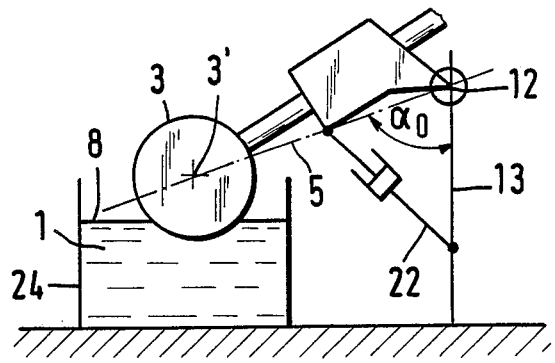
FIGS. 2a-2c show various elevations of the flask relative to the liquid bath according to the amount of fluid in the flask.
Figure 2B:
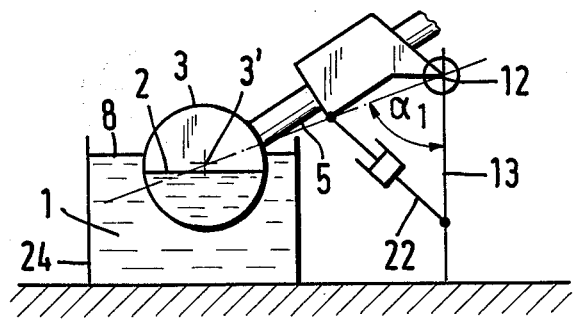
Figure 2C:
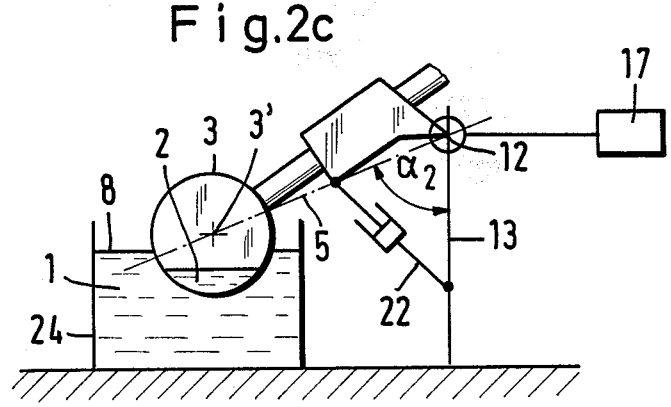

FIGS. 2a-2c indicate the use of the system according to the invention to concentrate the fluid 2 to a specific, preselected value. As shown in FIG. 2a, flask 3 is totally empty and only slightly penetrates into the liquid bath 1. Accordingly, it assumes a rather high elevation with respect to the liquid surface 8. The angle $\alpha_0$, measured between a line extending between the junction of flask center 3' and the axis of rotation 12, and the fixed reference line 13, assumes a relatively large value.

In FIG. 2b flask 3 is filled with the maximum amount of fluid medium 2 and, accordingly, sinks deeper into liquid bath 1. Thus, the angle $\alpha_1$ is correspondingly less than $\alpha_0$.

As the medium 2 is distilled within the rotary flask, the system becomes lighter and the rotary flask 3 rises in liquid 1. When the liquid reaches a predetermined level, as illustrated in FIG. 2c, the angle $\alpha$ will be equal to $\alpha_2$. When this angle is reached, adjustment means 17 will either: a) interrupt the operation of the system to enable the concentrate to be removed from the rotary flask; or, b) add additional fluid medium 2 to flask 3. In the latter instance, flask 3 once again descends into liquid 1 to the position of FIG. 2b. When angle $\alpha$ reaches $\alpha_1$, adjustment means 17 once again closes valve 18 to cut off the supply of fluid medium 2. This operation may continue until the desired concentration of medium 2 has been arrived at when angle $\alpha$ equals $\alpha_2$. At this point, the concentrate may be removed from flask 3 by known means.

Adjustment means 17 may also include means to count the number of times the system reaches $\alpha_1$ or $\alpha_2$, so as to cease operation of the equipment after it has reached this predetermined number. This enables the system to cease operation when the fluid medium 2 reaches a predetermined concentration.

As noted previously, it is possible to provide an adjustment means 17 which controls valve 18 such that the filling of the rotary flask remains approximately constant during the evaporation process. However, since the contents of the flask become more concentrated over a period of time, the mass of the rotary flask contents also increases. In order to preserve the maximum efficiency of the evaporation, the control system may decrease the reference value of the angle $\alpha_1$ each time the rotary flask arrives at angle $\alpha_2$. Accordingly, with every replenishing operation, rotary flask 3 receives somewhat more medium 2 to be processed than in the previous replenishing operation. Taking into account the specific type of medium 2 and its concentration, the control system may be implemented in such a manner that the filling of the rotary flask 3 remains approximately constant and therefore, due to the increase in concentration, the mass within the flask increases.

Following a specific number of oscillations between $\alpha_1$ and $\alpha_2$, the system may either be manually or automatically shut off and the concentrate removed from the flask 3.

The number of individual replenishing operations can be automatically counted by the adjustment means 17 and the reference value of angle $\alpha_1$ can be reduced by a predetermined amount at every further replenishment operation.

The replenishing control described above may also be accomplished by reducing the reference value of angle $\alpha_1$ as a function of the distillation time.

The reference angle $\alpha$ may also be utilized to generate a control signal when the flask has been filled to a predetermined amount so as to shut off any further flow of fluid into the flask. This averts any possibility of an overflow from the flask.

The system according to the invention is applicable to many fields of use, such as producing pure formalin from waste formalin in a simple and economical manner. An especial advantage is that the system may be operated unobserved for an extended period of time.

The foregoing description is provided for illustrative purposes only, and should not be construed as in any way limiting this invention, the scope of which is defined solely by the appended claims.

I claim:

1. A method of evaporating a fluid in a flask in a vacuum evaporating system comprising the steps of:
   (a) supplying a fluid to be distilled to a flask;
   (b) rotating the flask about an axis of symmetry;
   (c) buoyantly supporting the flask in a liquid bath;
   (d) drawing a vacuum within the flask;
   (e) evaporating the fluid within the flask;
   (f) sensing the elevation of the flask relative to the level of the liquid in the bath; and,
   (g) controlling the amount of fluid supplied to the flask in respnse to the elevation of the flask relative to the level of the liquid in the bath.

2. The method according to claim 1 further comprising the step of supporting the rotating flask such that it may also pivot about a pivot axis extending substantially perpendicular to its axis of symmetry.

3. The method according to claim 2 wherein in the elevation of the flask relative to the level of the liquid in the bath is sensed by measuring the angle $\alpha$ between a fixed reference line, and a line connecting the pivot axis and the center of the flask.

4. The method according to claim 3 wherein the step of sensing the elevation of the flask comprises the step of generating an electrical signal proportional to the angle $\alpha$.

5. The method according to claim 3 wherein the step of controlling the amount of fluid supplied to the flask comprises the steps of:
   (a) stopping the supply of fluid when the angle $\alpha$ reaches a first predetermined value; and,
   (b) removing the concentrate of the flask when the angle $\alpha$ reaches a second predetermined value.

6. The method according to claim 3 wherein the step of supplying a fluid to the flask comprises supplying the flask with a predetermined amount of fluid and wherein the step of controlling the amount of fluid comprises the step of adding an additional amount of fluid to the flask when the angle $\alpha$ reaches a first predetermined value.

7. The method according to claim 6 comprising the additional steps of:
   a) counting the number of times angle $\alpha$ reaches its first predetermined value; and,
   b) stopping the addition of fluid to the flask when angle $\alpha$ reaches its first value a predetermined number of times.

8. The method according to claim 6 wherein the same amount of fluid is added to the flask each time the angle $\alpha$ reaches its predetermined value.

9. The method according to claim 6 wherein decreasing amounts of fluid are added to the flask each time the angle $\alpha$ reaches its predetermined value such that the volume of the product remaining in the flask remains approximately constant.

10. The method according to claim 6 comprising the additional steps of: evaporating the liquid in the flask after buoyantly supporting the in the liquid bath; and shutting off the evaporation when the flask reaches a predetermined elevation relative to level of liquid in the bath.

11. The method according to claim 3 comprising the additional steps of:
    (a) supplying fluid to the flask until the angle $\alpha$ reaches a value of $\alpha_1$ from an initial value of $\alpha_0$ wherein $\alpha_1 < \alpha_0$;
    (b) evaporating at least a portion of the fluid in the flask;
    (c) adding additional fluid to the flask when angle $\alpha$ reaches a value of $\alpha_2$ wherein $\alpha_2 > \alpha_1$; and,
    (d) stopping the addition of fluid to the flask when angle $\alpha$ reaches a value of $\alpha_1$.

12. The method according to claim 11 further comprising the step of reducing the value of $\alpha_1$ each time additional fluid is added to the flask in such a manner that the volume of the product in the flask remains approximately constant.

13. The method according to claim 1 comprising the step of electronically controlling the amount of fluid supplied to the flask as a function of the elevation of the flask relative to the level of the liquid in the bath.

14. Apparatus for evaporating a fluid in a flask in a rotating vacuum evaporating system comprising:
    (a) a flask having an axis of symmetry;
    (b) rotating means to rotate the flask about its axis of symmetry;
    (c) means to supply the fluid to the interior of the flask;
    (d) means to draw a vacuum within the flask;
    (e) means to evaporate the fluid within the flask;
    (f) means to withdraw vapor from the interior of the flask;
    (g) a vessel containing a liquid path to buoyantly support the flask;
    (h) means for determining the elevation of the flask relative to the level of liquid in the bath; and
    (i) control means operatively connected to the means for determining the elevation of the flask to control the amount of fluid supplied to the flask in response to the elevation of the flask relative to the level of the liquid bath in the vessel.

15. Apparatus according to claim 14 wherein the control means includes means to stop the fluid supply to the flask.

16. Apparatus according to claim 14 wherein the control means includes means to remove concentrate from the flask when the flask reaches a predetermined elevation relative to the level of liquid in the bath.

17. Apparatus according to claim 14 further comprising pivotal support means for supporting the flask such that it may pivot about an axis extending generally perpendicular to its axis of symmetry and further comprising means to measure an angle $\alpha$ between a fixed reference line, and a line connecting the pivot axis and the center of the flask.

18. Apparatus according to claim 17 wherein the means for determining the elevation of the flask comprises means to generate an electrical signal proportional to the value of angle $\alpha$.

19. Apparatus according to claim 18 further comprising:
    (a) valve means interposed between the fluid supply means and the flask; and,
    (b) valve control means operatively connected to the valve means and the electrical signal to open and close the valve means as a function of angle $\alpha$.

20. Apparatus according to claim 17 wherein the pivotal support means comprises:
    (a) support rod means;
    (b) flask support means pivotally attached to the support rod means; and,
    (c) shock absorber means operatively connected between the flask support means and the support rod means.

21. Apparatus according to claim 19 wherein the control means further comprises means to supply fluid to the flask and wherein the valve control means controls the fluid such that the volume in the flask remains approximately constant during the evaporation process.

22. Apparatus according to claim 17 comprising means to intially supply the flask with a predetermined amount of fluid and wherein the control means comprises means for adding an additional amount of fluid to the flask when the angle $\alpha$ reaches a first predetermined value.

23. Apparatus according to claim 22 wherein the control means further comprises:
   (a) means for counting the number of times angle $\alpha$ reaches its first predetermined value; and
   (b) means for stopping the addition of fluid to the flask when angle $\alpha$ reaches its first value a predetermined number of times.

24. Apparatus according to claim 22 further comprising means to evaporate the liquid in the flask and means to shut off the evaporation means when the flask reaches a predetermined elevation relative to the level of liquid in the bath.

25. Apparatus according to claim 19 wherein the valve means is a magnetic valve.

26. Apparatus according to claim 14 wherein the control means comprises means to control the amount of fluid supplied to the flask as a function of the elevation of the flask relative to the level of the liquid in the bath.

27. Apparatus according to claim 14 wherein the control means comprises means to electronically control the sytem as a function of the elevation of the flask relative to the level of the liquid in the bath.

* * * * *